United States Patent [19]

Calabrese

[11] Patent Number: 4,515,153
[45] Date of Patent: May 7, 1985

[54] STABILIZER FOR CERVICAL COLLAR

[75] Inventor: Anthony Calabrese, Philadelphia, Pa.

[73] Assignee: Charles Greiner & Company, Inc., Westville, N.J.

[21] Appl. No.: 520,083

[22] Filed: Aug. 4, 1983

[51] Int. Cl.³ .............................................. A61H 1/02
[52] U.S. Cl. .................................... 128/75; 128/87 B; 128/DIG. 23
[58] Field of Search ................ 128/87 B, 75, DIG. 23

[56] References Cited

U.S. PATENT DOCUMENTS

| | | | |
|---|---|---|---|
| 2,223,276 | 11/1940 | Ward | 128/87 B |
| 2,692,595 | 10/1954 | Blair, Jr. | 128/87 B |
| 2,735,424 | 2/1956 | Benjamin | 128/87 B |
| 3,756,226 | 9/1973 | Calabrese et al. | 128/75 |
| 4,194,501 | 3/1980 | Watt | 128/87 B |
| 4,383,523 | 5/1983 | Schurman | 128/87 B |

Primary Examiner—John D. Yasko
Attorney, Agent, or Firm—Seidel, Gonda & Goldhammer

[57] ABSTRACT

A front piece adapted to overlie part of a person's chest is rigidly and removably connected to a front half of a cervical collar. A rear piece adapted to overlie part of a person's back is rigidly and removably connected to a rear half of a cervical collar. The front and rear pieces are connected to their half of the cervical collar by a plastic rivet. An adjustable strap innerconnects the front and rear pieces.

7 Claims, 7 Drawing Figures

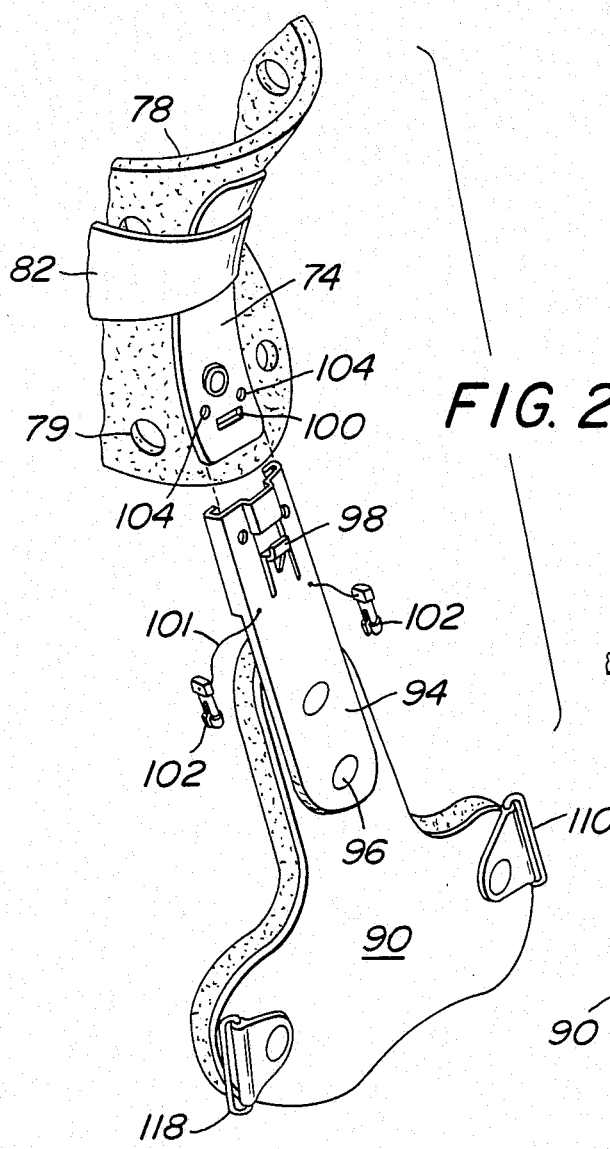
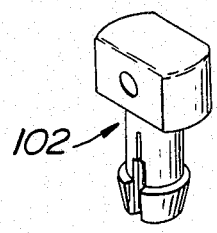
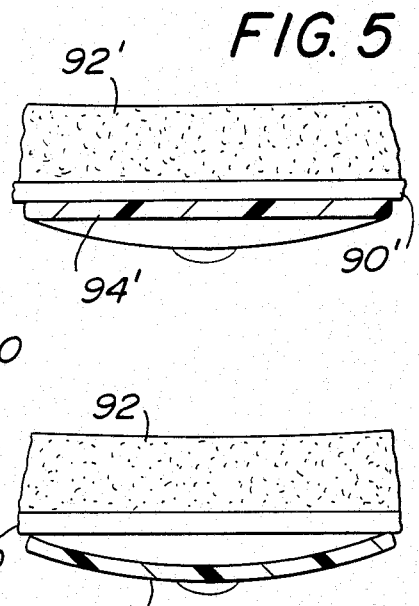
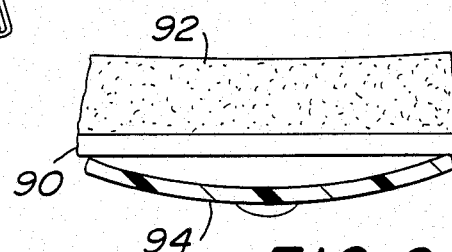
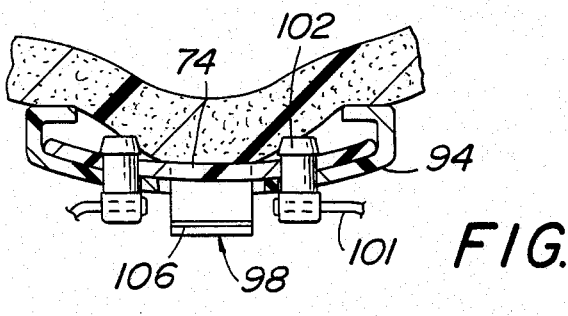

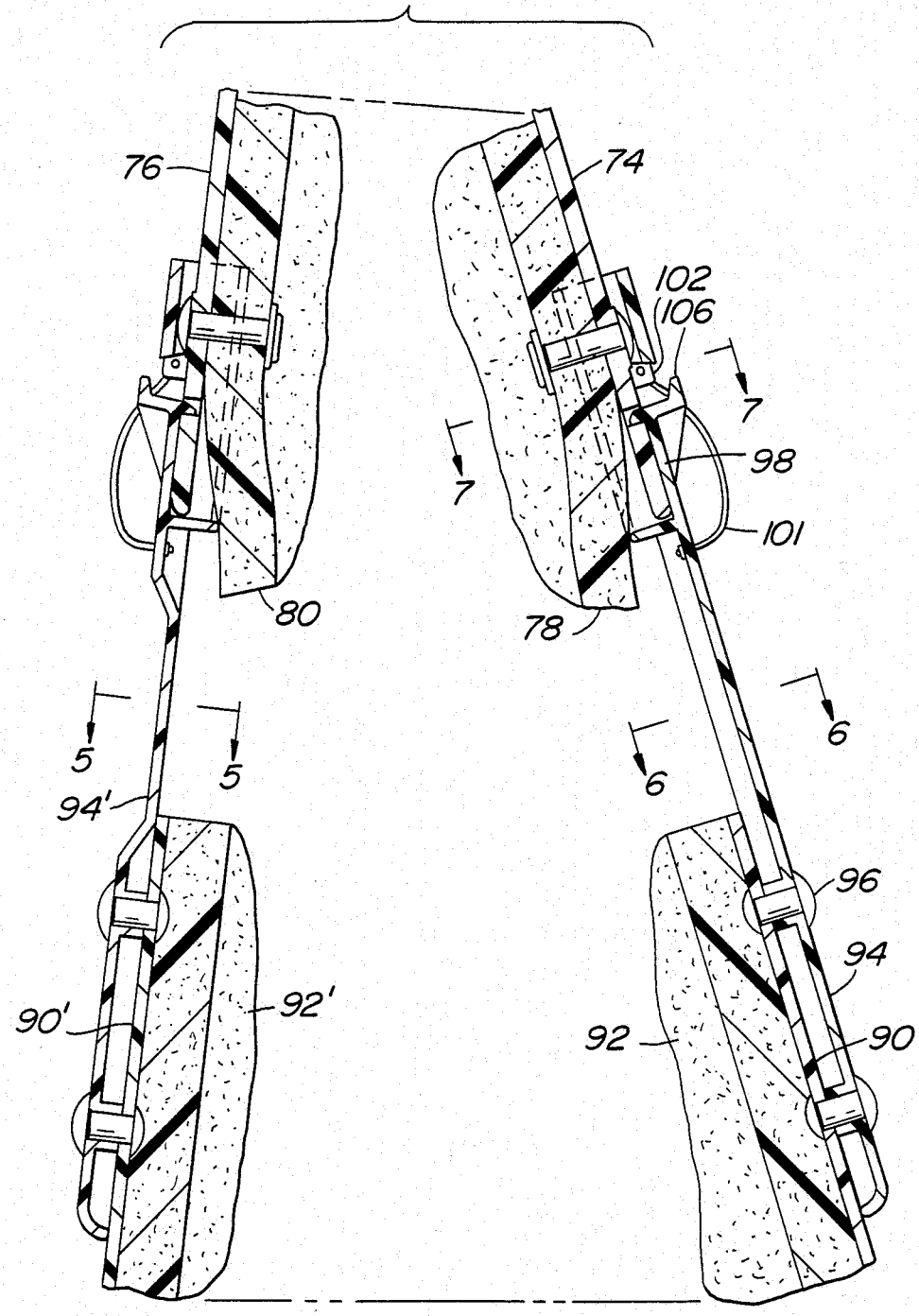

STABILIZER FOR CERVICAL COLLAR

BACKGROUND OF THE INVENTION

Cervical collars are well-known. See U.S. Pat. No. 3,756,226 issued on Sept. 4, 1973 and entitled Cervical Collar. The collar disclosed in said patent is comprised of body halves coupled together. Some injuries require more collar stability than others. Those injuries which require greater collar stability frequently alleviate over a short period of time. The amount of stability provided by the collar in said patent is insufficient for severe injuries.

The present invention is directed to a solution of the problem of how to provide temporary stabilization for a cervical collar with a structural interrelationship which minimizes access by the patient for separating the components.

SUMMARY OF THE INVENTION

The present invention is directed to a stabilizer for a certical collar. The stabilizer includes a front piece adapted to overlie part of a person's chest and a rear piece adapted to overlie part of a person's back. An adjustable strap means is provided for encircling a person's body and it removably innerconnects the front and rear pieces. A means is provided on the upper end of each piece for rigidly and removably connecting each piece to a discrete separate half of a cervical collar comprised of mating halves. The stabilizer is adapted to be interrelated with the collar for that period of time where greater stability is needed. Thereafter, the stabilizer may be removed from the collar so that the collar may be worn in a normal manner. The pieces and the collar halves are removably innerconnected in a manner which precludes or minimizes separation by the patient.

It is an object of the present invention to provide a novel stabilizer which may be removably attached to a cervical collar and which is difficult to remove by the patient.

Other objects and advantages will appear hereinafter.

For the purpose of illustrating the invention, there is shown in the drawongs a form which is presently preferred; it being understood, however, that this invention is not limited to the precise arrangements and instrumentalities shown.

FIG. 2 is an exploded view of the extension and the front collar half.

FIG. 3 is a sectional view taken along the line 3—3 in FIG. 1.

FIG. 4 is a perspective view of the split rivet.

FIG. 5 is a sectional view taken along the line 5—5 in FIG. 3.

FIG. 6 is a sectional view taken along the line 6—6 in FIG. 3.

FIG. 7 is a sectional view taken along the line 7—7 in FIG. 3.

DETAILED DESCRIPTION

Figure 1:
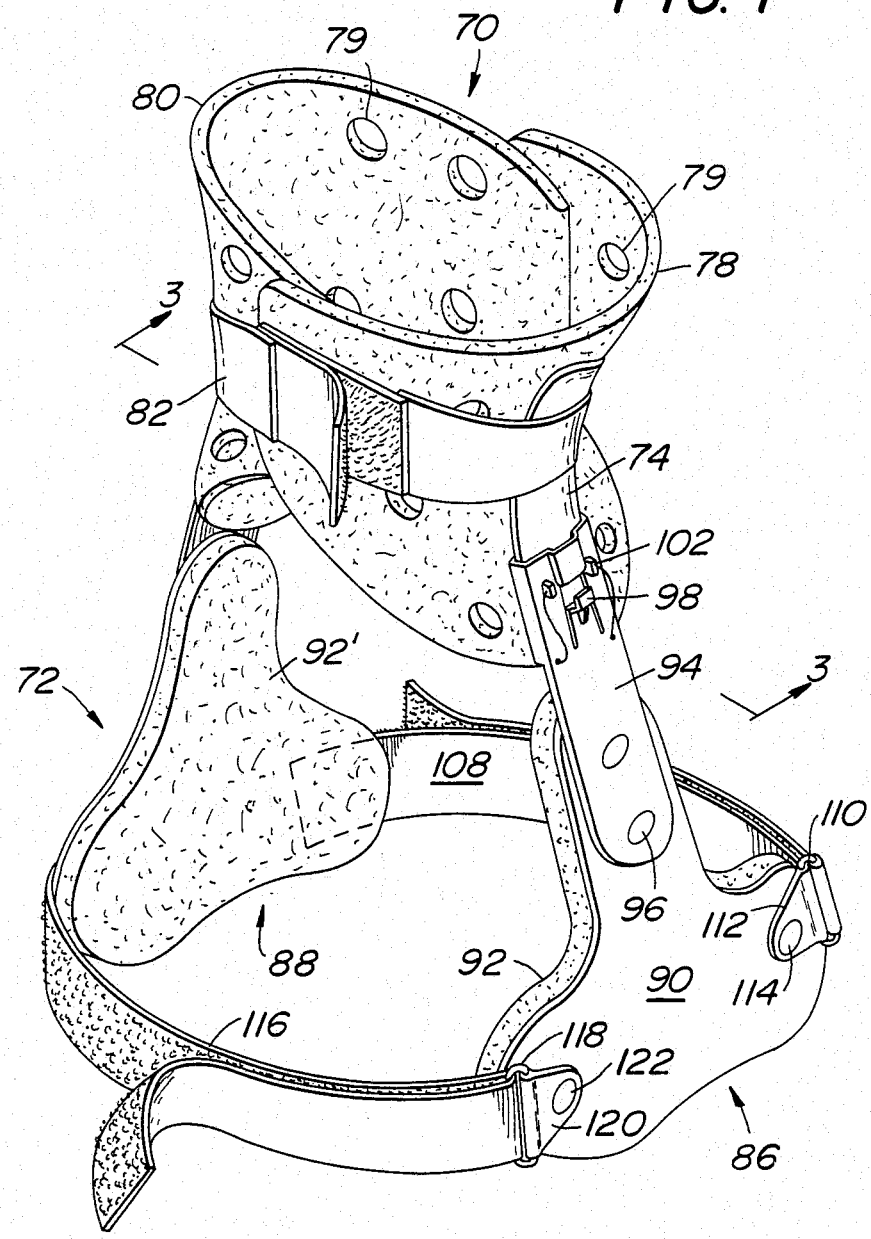
FIG. 1 is a perspective view of a cervical collar with the stabilizer of the present invention attached thereto.

Referring to the drawing in detail, wherein like numerals indicate like elements, there is shown in FIG. 1 a cervical collar designated generally as 70 and provided with a stabilizer designated generally as 72. The stabilizer 72 is particularly designed for use with a cervical collar as disclosed in U.S. Pat. No. 3,756,226 and may be of different sizes such as small, medium and large. The collar 70 includes a rigid reinforcing member 74 on a front half 78 and a rigid reinforcing member 76 in a rear half 80. The body halves 78 and 80 of the cervical collar are coupled together by a strap means 82 when in use. As disclosed in said patent, each body half 78, 80 is preformed from a soft, flexible closed cell polymeric material. The body halves 78, 80 are preferably provided with air holes 79.

The stabilizer 72 includes a front piece 86 adapted to overlie part of a person's chest and a rear piece 88 adapted to overlie a person's back. The front piece and rear piece are identical except as will be made clear hereinafter. Hence, only the front piece 86 will be described in detail. Corresponding primed numerals are provided on the rear piece.

The front piece 86 includes a substrate 90 of rigid material having a generally T-shape. The substrate 90 is preferably made from a polymeric plastic material such as ABS. A liner 92 is adhesively or otherwise secured to the curved inner surface of substrate 90. The liner 92 is preferably made from a closed-cell foam polyethylene so as to have the following attributes: uniform thickness, non-toxic, low specific gravity of about 0.04, non-corosive, and will not burn but will melt. The shape of liner 92 corresponds to the shape of substrate 90.

A connecting member 94 is fixedly connected to the center leg of substrate 90 in any convenient manner such as by plastic rivets 96. The connecting member 94 is preferably made from a softer or more flexible plastic material than the substrate 90 and may be made from material such as polyethylene.

As shown more clearly in FIGS. 6 and 7, member 94 is arcuate at its lower end and channel-shaped at its upper end. Member 94 is telescoped over member 74 until a tongue on member 98 snaps into slot 100 on member 74. Member 98 acts like a hinge and is integral at one end only with the member 94.

It is desirable to removably innerconnect the front and rear pieces to the collar 10 in a manner so that it is not readily removable by the patient. In this regard, at least one and preferably two plastic rivets 102 are carried by member 94 by way of a flexible string 101. The rivets are easily pushed and snapped into a hole 104 on member 74. As shown more clearly in FIG. 4, each rivet has a head provided with flats on opposite sides together with a hole therethrough to facilitate connection to the string 101. The shanks of the rivets 102 are split. The rivets are easily force-fit into the holes 102 by application of finger-pressure. However, a tool such as a pair of pliers is needed to pull out the rivets 102. When the rivets 102 are removed, members 74 and 94 are easily separated by pulling on the tab 106 so as to cause member 98 to withdraw from the slot 100. The channel-shape at the upper end of member 94 assures that the tongue on member 98 will be alligned with slot 100 when member 94 is telescoped onto member 74.

The rear piece 88 is identical with the front piece 86 except as follows. Corresponding elements are provided with corresponding primed numerals. Member 94' is thinner and therefore more flexible than member 94. Greater rigidity is needed on the front piece 86 as compared with the rear piece 88.

A strap 108 has one end fixedly secured to the substrate 90' on rear piece 88. The strap 108 extends through a loop 110 on the front piece 86 and then overlies itself. The loop 110 is preferably supported by a bracket 112 which in turn is secured to the substrate 90 in any convenient manner such as by plastic rivet 114. Juxtaposed surfaces of the strap 108 are provided with adjustable fasteners which preferably are of the Velcro type.

A strap 116 is similarly provided to interconnect the front and rear pieces 86 and 88 on the opposite side from the strap 108. One end of strap 116 is fixedly secured to the substrate 90'. An intermediate portion of strap 116 extends through a loop 118 and then overlies itself with adjustable fasteners as described above. Loop 118 is supported by a bracket 120 which in turn is secured to the substate 90 by plastic rivet 122.

The collar 70 may be worn in a conventional manner. In connection with a particular injury, the collar 70 may need added stabilization. The front and rear pieces are attached to the collar 70 as described above. Thereafter, the front and rear pieces are coupled together by straps 108 and 116. If desired, one signal strap may be utilized by innerconnecting the ends of the straps attached to the substrate 90'. When no longer needed, the front and rear pieces 86, 88 are disconnected while the collar 10 remains on the person for so long as required in accordance with medical advice.

The rivets 102 can only be removed by hand tools such as a pair of plyers. A person wearing the collar cannot see or manipulate the rivets 102 without great difficulty. The strings 101 prevent the rivet 102 from becomming lost when removed. The heads of the rivets 102 may have a plurality of flats such as flats produced when the head is hexagon or octagon shaped.

All of the rivets such as rivets 96 and the loops such as loop 110 are preferably made from plastic. Hence, the patient may be X-rayed with the present invention mounted on the patient. There are no metal parts which will show up on X-rays and interfere with evaluation of the X-rays.

The present invention may be embodied in other specific forms without departing from the spirit or essential attributes thereof and accordingly, reference should be made to the appended claims, rather than to the foregoing specification, as indicating the scope of the invention.

I claim:

1. A cervical collar comprising discrete front and back halves adapted to partially overlap one another, said halves being made from a soft, flexible polymeric plastic material, strap means for securing the halves in overlapping relation, a stabilizer for said collar including a front piece adapted to overlie part of a person's chest and a rear piece adapted to overlie part of a person's back, adjustable strap means for encircling a portion of a person's body and removably innerconnecting said front piece and said rear piece, means on the upper end of said front and rear pieces for removably connecting the front and rear pieces to their associated collar half, said last-mentioned means including at least one plastic rivet having a non-circular head and being removable by a hand tool.

2. A collar in accordance with claim 1 wherein each platic rivet is connected to its associated front and rear piece by a string.

3. A collar in accordance with claim 1 wherein each collar half having a horizontal slot, said last mentioned means including a hinged projection on each of said front and rear pieces, each projection having a portion adapted to enter one of said slots.

4. A stabilizer for a cervical collar comprising a plastic front piece in the shape of an inverted T and adapted to overlie part of a person's chest, a plastic rear piece in the shape of an inverted T and adapted to overlie part of a person's back, adjustable strap means for encircling a portion of a body and for removably interconnecting said front piece and rear piece, a connecting member fixedly attached to the upper end of said front piece for rigidly and removably connecting said front piece to the front half of a cervical collar without tools, a connecting member attached to the upper end of the rear piece for rigidly and removably connecting said rear piece to a cervical collar without tools, each connecting member having a portion adapted to enter into a slot on a cervical collar and a lip to facilitate withdrawal of said portion from its associated slot by finger manipulation, each of said portions being integral in one piece at one end with its associated connecting member.

5. A stablizer in accordance with claim 4 wherein the connecting member on said front piece is more rigid than the connecting member on said rear piece, and the components of the front and rear pieces being coupled together by plastic rivets.

6. A stabilizer in accordance with claim 4 wherein said connecting member on said front piece has a plastic rivet for removably connecting the front piece to a cervical collar by finger manipulation, said plastic rivet being constructed so as to require a hand tool for removal.

7. A stabilizer in accordance with claim 4 including a cervical collar, said cervical collar including discrete front and back halves adapted to partially overlap one another, said halves being made from a soft, flexible polymeric plastic material, strap means for securing the halves in overlapping relation, each of said collar halves having a rigid downwardly extending reinforcement member adjacent the bight of its associated collar half and telescopically coupled to an associated connecting member of said stabilizer.

* * * * *